(12) United States Patent
Koike et al.

(10) Patent No.: US 11,278,212 B2
(45) Date of Patent: Mar. 22, 2022

(54) INTRACRANIAL PRESSURE ESTIMATING METHOD AND INTRACRANIAL PRESSURE ESTIMATING DEVICE

(71) Applicants: ICHIKAWA ELECTRIC CO., LTD., Hamura (JP); SHINSHU UNIVERSITY, Matsumoto (JP)

(72) Inventors: Norio Koike, Hamura (JP); Satoshi Yasumoto, Hamura (JP); Jun Nakano, Hamura (JP); Yukio Sai, Hamura (JP); Kenji Furihata, Matsumoto (JP); Tetsuya Goto, Matsumoto (JP); Kazuhiro Hongo, Matsumoto (JP)

(73) Assignees: ICHIKAWA ELECTRIC CO., LTD., Hamura (JP); SHINSHU UNIVERSITY, Nagano (JP)

( * ) Notice: Subject to any disclaimer, the term of this patent is extended or adjusted under 35 U.S.C. 154(b) by 329 days.

(21) Appl. No.: 16/309,424

(22) PCT Filed: Jun. 12, 2017

(86) PCT No.: PCT/JP2017/021589
§ 371 (c)(1),
(2) Date: Dec. 12, 2018

(87) PCT Pub. No.: WO2017/217353
PCT Pub. Date: Dec. 21, 2017

(65) Prior Publication Data
US 2019/0328248 A1    Oct. 31, 2019

(30) Foreign Application Priority Data
Jun. 17, 2016    (JP) .............................. JP2016-120708

(51) Int. Cl.
*A61B 5/03*    (2006.01)
*A61B 5/00*    (2006.01)

(52) U.S. Cl.
CPC .............. *A61B 5/031* (2013.01); *A61B 5/036* (2013.01); *A61B 5/7278* (2013.01)

(58) Field of Classification Search
CPC ....... A61B 5/031; A61B 5/036; A61B 5/7278; A61B 5/7235; A61B 5/7225; A61B 5/6817; A61B 5/024
See application file for complete search history.

(56) References Cited

U.S. PATENT DOCUMENTS 5,117,835 A    6/1992    Mick
5,964,705 A    10/1999   Truwit et al.
(Continued)

FOREIGN PATENT DOCUMENTS

JP    H05-300880 A    11/1993
JP    H08-084704 A    4/1996
(Continued)

OTHER PUBLICATIONS

Takizawa; Hideo, "Changes in Cerebrospinal Fluid Pulse Wave Spectrum Associated with Raised Intracranial Pressure", Neurosurgery vol. 20, No. 3 1987 (Year: 1987).*
(Continued)

*Primary Examiner* — Sean P Dougherty
*Assistant Examiner* — Alexander H Connor
(74) *Attorney, Agent, or Firm* — Oliff PLC (57) ABSTRACT

An intracranial pressure estimating method includes: an acquisition step (S10) of acquiring time-series data on external ear canal pressure pulse waves of a subject; an analysis step (S12) of analyzing external ear canal pressure pulse wave data obtained by digitalizing the time-series data on the external ear canal pressure pulse waves, to calculate a first formant frequency of the external ear canal pressure pulse wave data; a correction step (S13) of correcting the calculated first formant frequency based on personal infor-
(Continued)

mation on the subject to calculate a corrected value; and an estimation step (S14) of calculating an estimated value of an intracranial pressure based on the calculated corrected value.

9 Claims, 9 Drawing Sheets

(56) References Cited

U.S. PATENT DOCUMENTS

| | | | |
|---|---|---|---|
| 6,026,316 | A | 2/2000 | Kucharczyk et al. |
| 6,061,587 | A | 5/2000 | Kucharczyk et al. |
| 6,129,682 | A | 10/2000 | Borchert et al. |
| 6,272,370 | B1 | 8/2001 | Gillies et al. |
| 6,487,437 | B1 | 11/2002 | Viswanathan et al. |
| 6,537,232 | B1 | 3/2003 | Kucharczyk et al. |
| 6,560,475 | B1 | 5/2003 | Viswanathan |
| 6,587,706 | B1 | 7/2003 | Viswanathan |
| 7,048,716 | B1 | 5/2006 | Kucharczyk et al. |
| 7,505,807 | B1 | 3/2009 | Kucharczyk et al. |
| 2002/0095087 | A1 | 7/2002 | Mourad et al. |
| 2002/0161304 | A1 | 10/2002 | Eide |
| 2003/0100845 | A1 | 5/2003 | Eide |
| 2003/0199784 | A1 | 10/2003 | Lenhardt |
| 2003/0220577 | A1 | 11/2003 | Bartels et al. |
| 2003/0220584 | A1 | 11/2003 | Honeyager et al. |
| 2004/0049105 | A1* | 3/2004 | Crutchfield ............... A61B 8/56 600/407 |
| 2004/0059220 | A1 | 3/2004 | Mourad et al. |
| 2005/0015009 | A1* | 1/2005 | Mourad ............... A61B 5/7267 600/438 |
| 2006/0079773 | A1 | 4/2006 | Mourad et al. |
| 2006/0100530 | A1 | 5/2006 | Kliot et al. |
| 2006/0206037 | A1 | 9/2006 | Braxton |
| 2007/0016031 | A1 | 1/2007 | Mourad et al. |
| 2007/0060835 | A1 | 3/2007 | Eide |
| 2007/0060836 | A1 | 3/2007 | Eide |
| 2008/0139959 | A1 | 6/2008 | Miethke et al. |
| 2009/0149751 | A1 | 6/2009 | Mourad et al. |
| 2009/0326411 | A1 | 12/2009 | Eide |
| 2010/0081893 | A1 | 4/2010 | Jarvik et al. |
| 2010/0087728 | A1 | 4/2010 | Jarvik et al. |
| 2012/0108918 | A1 | 5/2012 | Jarvik et al. |
| 2014/0039279 | A1 | 2/2014 | Jarvik et al. |
| 2014/0276181 | A1* | 9/2014 | Sun ..................... A61B 5/369 600/544 |
| 2015/0351716 | A1* | 12/2015 | Weinberg ............... A61B 8/54 600/407 |

FOREIGN PATENT DOCUMENTS

| | | |
|---|---|---|
| JP | 2000-121467 A | 4/2000 |
| JP | 2001-346767 A | 12/2001 |
| JP | 2002-513310 A | 5/2002 |
| JP | 2004-528104 A | 9/2004 |
| JP | 2006-505300 A | 2/2006 |
| JP | 2006-102163 A | 4/2006 |
| JP | 2006-230504 A | 9/2006 |
| JP | 2006-526487 A | 11/2006 |
| JP | 2007-301215 A | 11/2007 |
| JP | 2008-237847 A | 10/2008 |
| JP | 2008-539811 A | 11/2008 |
| JP | 2008-543352 A | 12/2008 |
| JP | 2010-017317 A | 1/2010 |
| JP | 2010-187928 A | 9/2010 |
| JP | 2013-102784 A | 5/2013 |
| JP | 2014-204879 A | 10/2014 |
| JP | 2016-059755 A | 4/2016 |
| JP | 2016059755 A * | 4/2016 |

OTHER PUBLICATIONS

Jan. 17, 2020 Extended European Search Report issued in European Patent Application No. 17813249.4.
Marek Czosnyka, et al.; "Hydrodynamic Properties of Extraventricular Drainage Systems"; Neurosurgery; vol. 52; No. 3; Mar. 2003; pp. 619-623.
Rohlfing, Torsten et al. "Effect of Changing Patient Position from Supine to Prone on the Accuracy of a Brown-Roberts-Wells Stereotactic Head Frame System." Neurosurgery, vol. 52, 610-618, 2003.
Cheong, Jong Woo et al. "Effectiveness of Preoperative Extra-Ventricular Drainage in Poor Grade Aneurysmal Subarachnoid Hemmorrhage." Korean J Cerebrovascular Disease, vol. 4, 52-57, 2002.
Fujioka, Shoda et al. "The Usefulness of Lumbar Epidural Pressure as an Index of Intracranial Pressure." Neurologia medico-chirurgica, vol. 29, 484-489, 1989.
Matsuyama, Masayuki. "Recording of the Effects on the External Auditory Canal Pressure Waves of Intracranial Pressure Pulse Waves and Blood Pressure Waves." Keio Medical Society, vol. 72, 497-509, 1995.
Zou, Rui et al. "Intracranial Pressure Waves: Characterization of a Pulsation Absorber with Notch Filter Properties Using Systems and Analysis." J. Neurosurg Pediatrics, vol. 2., 83-94, 2008.
De Kleine, et al. "The Behavior of Spontaneous Otoacoustic Emissions During and After Postural Changes." J. Acoustical Society of America, vol. 107, 3308-3316, 2000.
Ohyama, Kenji. "Preface for the Special Issue on 'Otoacoustic Emissions: OAEs.' Spontaneous Otoacoustic Emissions." Journal of the Acoustical Society of Japan, vol. 50, 739-742, 1994.
Sep. 19, 2017 International Search Report issued in International Patent Applicaton No. PCT/JP2017/021589.
Oct. 14, 2021 Office Action issued in Korean Patent Application No. 10-2018-7037888.
Jun. 22, 2021 Office Action issued in Japanese Patent Application No. 2018-523886.
Jun. 29, 2021 Office Action issued in Chinese Patent Application No. 201780037751.2.

* cited by examiner

| No. | MICP [cmH$_2$0] | f1 [Hz] | AGE | M=1/F=2 |
|---|---|---|---|---|
| 1 | 6.5 | 4.1 | 55 | 1 |
| 2 | 10 | 4.7 | 62 | 2 |
| 3 | 10 | 4.9 | 51 | 2 |
| 4 | 10 | 4.9 | 51 | 2 |
| 5 | 13.8 | 4.5 | 42 | 1 |
| 6 | 15 | 4.1 | 49 | 2 |
| 7 | 16.4 | 4.3 | 53 | 1 |
| 8 | 18 | 4.9 | 67 | 1 |
| 9 | 19.9 | 5.1 | 62 | 2 |
| 10 | 23.3 | 4.1 | 14 | 1 |
| 11 | 30 | 4.9 | 42 | 2 |
| 12 | 30 | 4.5 | 23 | 1 |
| 13 | 36 | 4.7 | 47 | 1 |
| 14 | 37 | 4.7 | 54 | 1 |
| 15 | 40 | 4.5 | 29 | 1 |
| 16 | 45 | 5.3 | 54 | 1 |
| 17 | 46 | 5.5 | 23 | 1 |
| 18 | 64 | 5.3 | 47 | 1 |
| 19 | 70 | 7.0 | 73 | 2 |

INTRACRANIAL PRESSURE ESTIMATING METHOD AND INTRACRANIAL PRESSURE ESTIMATING DEVICE

TECHNICAL FIELD

The present invention relates to an intracranial pressure estimating method and an intracranial pressure estimating device.

BACKGROUND ART

Many organs and nerves, including the brain, are concentrated in the head of a human, and measuring biological information in this site is very significant in terms of health control and disease prevention. In particular, intracranial pressure (ICP) is always maintained constant due to biological homeostasis, and it is known that the increased or decreased intracranial pressure may cause a fatal severe disease in some cases. Moreover, the intracranial pressure is used as an index for therapy and diagnosis of brain damage, stroke, and intracranial hemorrhage. Thus, it is particularly significant to find the establishment of an intracranial pressure measuring method.

As conventional intracranial pressure measuring methods, a method of placing a piezoelectric sensor directly under the cranium bones (PTL 1, NPL 1 and 2) and a method of directly inserting a tube into the lateral ventricle and measuring pressure of a water column rising therefrom (PTL 2, NPL 3) have been generally known. In each of the methods, however, a hole needs to be drilled in the cranium bone or a sensor or a tube needs to be placed inside the cranium bone, which is highly invasive for subjects and requires subjects to take a complete rest during measurement. It is difficult to measure and evaluate the intracranial pressure by only one momentary value, and it is a common practice to measure continuous values for a certain period of time. There is a risk that subjects may be infected with fungus during the measurement, and the countermeasures need to be taken into consideration. Thus, studies have been made on many intracranial pressure measuring technologies that put less burden on subjects, that is, low-invasive.

Examples of the intracranial pressure measuring methods reported so far include a technology of injecting a contrast medium in the cranium bone of a subject and measuring the intracranial pressure by NMR measurement (PTL 3). Another report is a technology of injecting a contrast medium in the cranium bone of a subject, generating fine bubbles in this site, acquiring low frequency response, and analyzing resonant frequency (PTL 4). Another report is a technology of irradiating the eyeball of a subject with infrared rays and performing FT-IR analysis of reflected light to measure the intracranial pressure (PTL 5 to 7). Another report as a technology of non-invasively detecting biological information from a site near the brain is a technology of measuring pulse waves in the ear canal (PTL 8 to 15). It has been reported to measure acoustic data on the artery blood pressure and the blood flow of middle cerebral artery and take a non-linear correlation therebetween to calculate the intracranial pressure (PTL 16). In medical animal testing, it has been known from simultaneous recording of ear canal pressure waves, artery pressure waves, and intracranial pressure waves of cats, the amplitude of the ear canal pressure increases when the blood pressure rises, and the propagation time from the artery pressure waves to the ear canal pressure waves is shortened when the intracranial pressure rises (NPL 4), and it has been known from the measurement of artery pressure waves (which is main component of pressure waves in ear canal) and intracranial pressure waves of dogs that a notch appears on a transfer function and is affected by change in pressure in the brain (cerebrospinal pressure) (NPL 5).

To deal with the technical problems inherent to the above-mentioned technologies, the inventors of the invention have proposed a method of measuring carotid pulse waves and external ear canal pressure pulse waves to estimate the intracranial pressure based on amplitude information and waveform information on both the pulse waves (PTL 17).

CITATION LIST

Patent Literature

PTL 1: J-T-2008-539811
PTL 2: JP-A-5-300880
PTL 3: JP-A-2001-346767
PTL 4: JP-A-2006-230504
PTL 5: JP-T-2002-513310
PTL 6: JP-A-2007-301215
PTL 7: JP-T-2008-543352
PTL 8: JP-A-8-84704
PTL 9: JP-A-2000-121467
PTL 10: JP-T-2004-528104
PTL 11: JP-A-2006-102163
PTL 12: JP-T-2006-505300
PTL 13: JP-A-2008-237847
PTL 14: JP-A-2010-17317
PTL 15: JP-A-2010-187928
PTL 16: JP-T-2006-526487
PTL 17: JP-A-2013-102784

Non-Patent Literature

NPL 1: Neurosurgery, 2003 March; 52(3): 619-23; discussion 623
NPL 2: Korean J Cerebrovasc Dis, 2002 March; 4(1): 52-57. Korean
NPL 3: Neurologia medico-chirurgica, 29(6), 484-489, 1989 Jun. 15
NPL 4: Keio Medical Society, vol. 72(6), pp. 497-509, 1995
NPL 5: J. Neurosurg Pediatrics, vol. 2, pp. 83-94, 2008

SUMMARY OF INVENTION

Technical Problem

The importance of intracranial pressure measurement with a non-invasive and simple configuration is particularly recognized in emergency medical care and control of critically ill patients, such as patients with disturbance of consciousness due to brain disorder. For intracranial pressure measurement in such medical cares, a device used for the measurement needs to be able to measure the intracranial pressure non-invasively with as simple a configuration as possible.

The invention has been made in view of the above-mentioned problems. The invention can provide an intracranial pressure estimating method and the like capable of estimating intracranial pressure in real time without putting burden on subjects by using a non-invasive and simple device.

Solution to Problem

APPLICATION EXAMPLE 1

According to this application example, there is provided an intracranial pressure estimating method for estimating an intracranial pressure from time-series data on external ear canal pressure pulse waves, the method including:

an acquisition step of acquiring time-series data on external ear canal pressure pulse waves of a subject;

an analysis step of analyzing external ear canal pressure pulse wave data obtained by digitalizing the time-series data on the external ear canal pressure pulse waves to calculate a first formant frequency of the external ear canal pressure pulse wave data;

a correction step of correcting the first formant frequency based on personal information on the subject to calculate a corrected value; and an estimation step of calculating an estimated value of the intracranial pressure based on the corrected value.

According to this application example, the intracranial pressure can be estimated based on external ear canal pressure pulse waves that can be measured by a non-invasive and simple device, and hence the intracranial pressure estimating method capable of estimating the intracranial pressure in real time without putting burden on subjects can be implemented. Further, the first formant frequency of the external ear canal pressure pulse wave data is corrected based on the personal information on the subject, and the obtained corrected value is used to calculate the estimated value of the intracranial pressure. Thus, an intracranial pressure estimating method capable of accurately estimating the intracranial pressure can be implemented.

Application Example 2

In the above-mentioned intracranial pressure estimating method, the analysis step may include analyzing data obtained by subjecting the external ear canal pressure pulse wave data to high-pass filter processing to calculate the first formant frequency.

Consequently, influence of breathing and heartbeat of subjects can be reduced, and hence an intracranial pressure estimating method capable of accurately estimating the intracranial pressure can be implemented.

Application Example 3

In the above-mentioned intracranial pressure estimating method, the estimation step may include calculating an estimated value PICP of the intracranial pressure based on the following equation:

$$PICP = A \cdot \ln(Xf1) + B$$

where A and B are constants, and Xf1 is the corrected value.

Consequently, an intracranial pressure estimating method capable of accurately estimating the intracranial pressure can be implemented.

Application Example 4

In the above-mentioned intracranial pressure estimating method, the correction step may include calculating the corrected value Xf1 based on the following equation:

$$Xf1 = f1 + \beta_1 \cdot \ln(K/Age) + \beta_2 \cdot FM$$

where f1 is the first formant frequency, $\beta_1$, K, and $\beta_2$ are constants, Age is the age of the subject, and FM is the sex of the subject (0 for male and 1 for female).

Consequently, an intracranial pressure estimating method capable of accurately estimating the intracranial pressure can be implemented.

Application Example 5

According to this application example, there is provided an intracranial pressure estimating device including:

an external ear canal pressure pulse wave sensor that detects external ear canal pressure pulse waves of a subject; and an arithmetic unit that estimates an intracranial pressure from time-series data on the external ear canal pressure pulse waves, wherein the arithmetic unit analyzes external ear canal pressure pulse wave data obtained by digitalizing the time-series data on the external ear canal pressure pulse waves, calculates a first formant frequency of the external ear canal pressure pulse wave data, corrects the first formant frequency based on personal information on the subject to calculate a corrected value, and calculates an estimated value of the intracranial pressure based on the corrected value.

According to this application example, the intracranial pressure can be estimated based on external ear canal pressure pulse waves that can be measured by a non-invasive and simple device, and hence the intracranial pressure estimating device capable of estimating the intracranial pressure in real time without putting burden on subjects can be implemented. Further, the first formant frequency of the external ear canal pressure pulse wave data is corrected based on the personal information on the subject, and the obtained corrected value is used to calculate the estimated value of the intracranial pressure. Thus, an intracranial pressure estimating device capable of accurately estimating the intracranial pressure can be implemented.

DESCRIPTION OF EMBODIMENTS

Preferred embodiments of the invention are described in detail below with reference to the drawings. The drawings to be referred to are illustrative. Note that the following embodiments do not unduly limit the scope of the invention as stated in the claims. In addition, all of the elements described in connection with the following embodiments should not necessarily be taken as essential requirements of the invention.

1. Configuration

Figure 1:
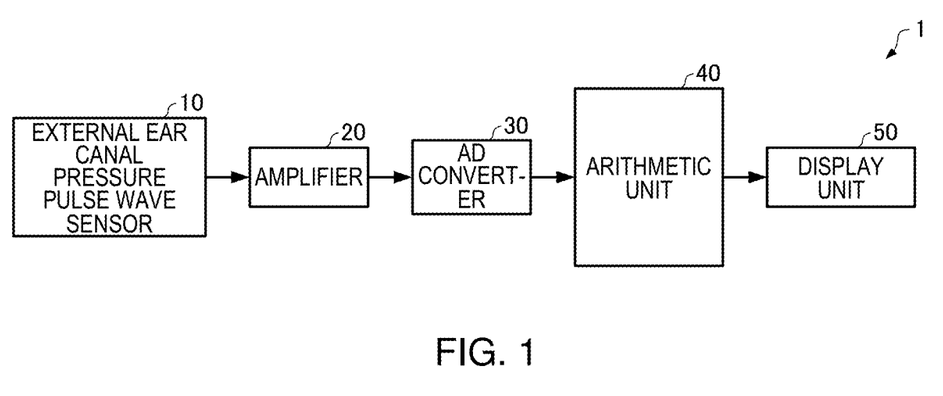
FIG. 1 is a functional block diagram illustrating a configuration example of an intracranial pressure estimating device according to an embodiment of the invention.

FIG. 1 is a functional block diagram illustrating a configuration example of an intracranial pressure estimating device according to an embodiment of the invention. An intracranial pressure estimating device 1 includes an external ear canal pressure pulse wave sensor 10, an amplifier 20 (AC amplifier), an AD converter 30, an arithmetic unit 40 having an arithmetic processing unit (processor) and a storage unit, and a display unit 50.

The external ear canal pressure pulse wave sensor 10 detects external ear canal pressure pulse waves. The external ear canal pressure pulse waves (ear canal pulse wave sound pressure) detected by the external ear canal pressure pulse wave sensor 10 are amplified by the amplifier 20, converted into digital data by the AD converter 30, and output to the arithmetic unit 40. As the external ear canal pressure pulse wave sensor 10, a sound sensor or a pressure sensor can be used.

Figure 2:
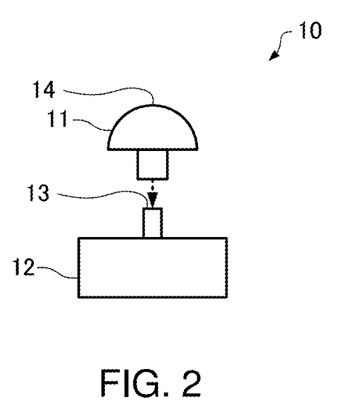
FIG. 2 is a diagram illustrating a configuration example of an external ear canal pressure pulse wave sensor.

FIG. 2 is a diagram illustrating a configuration example of the external ear canal pressure pulse wave sensor 10. The external ear canal pressure pulse wave sensor 10 includes a sealed portion 11 that seals the ear canal to form a sealed space, and a microphone 12 that detects sound pressure in the sealed space as ear canal pulse wave sound pressure. The sealed portion 11 has a substantially hemispherical shape and is provided with a sound hole 14 communicating to a sound hole 13 in the microphone 12. When detecting the external ear canal pressure pulse waves, the sound hole 14 is mounted to communicate to the ear canal. The sealed portion 11 and the microphone 12 are coupled such that the distal end of the sound hole 13 in the microphone 12 communicates to the sound hole 14 in the sealed portion 11. As the sealed portion 11, for example, an ear tip made of resin or an ear tip combined with plastic material may be employed. An air hole may be provided in the sealed portion 11 and may be sealed when the insertion to the ear canal is completed. As the microphone 12, for example, a condenser electret microphone may be employed.

Referring back to FIG. 1, the arithmetic unit 40 analyzes external ear canal pressure pulse wave data (output signal of AD converter 30) obtained by digitalizing time-series data on the external ear canal pressure pulse waves detected by the external ear canal pressure pulse wave sensor 10, calculates a first formant frequency of the external ear canal pressure pulse wave data, corrects the calculated first formant frequency based on the age and the sex of the subject (personal information on subject) to calculate a corrected value, and calculates an estimated value of the intracranial pressure based on the calculated corrected value. The arithmetic unit 40 may analyze data obtained by subjecting the external ear canal pressure pulse wave data to high-pass filter processing to calculate the first formant frequency.

The display unit 50 (display) displays the external ear canal pressure pulse wave data and arithmetic results of the arithmetic unit 40 (estimated value of intracranial pressure). As the display unit 50, for example, a liquid crystal display or a CRT display can be employed.

2. Principle

Figure 3:
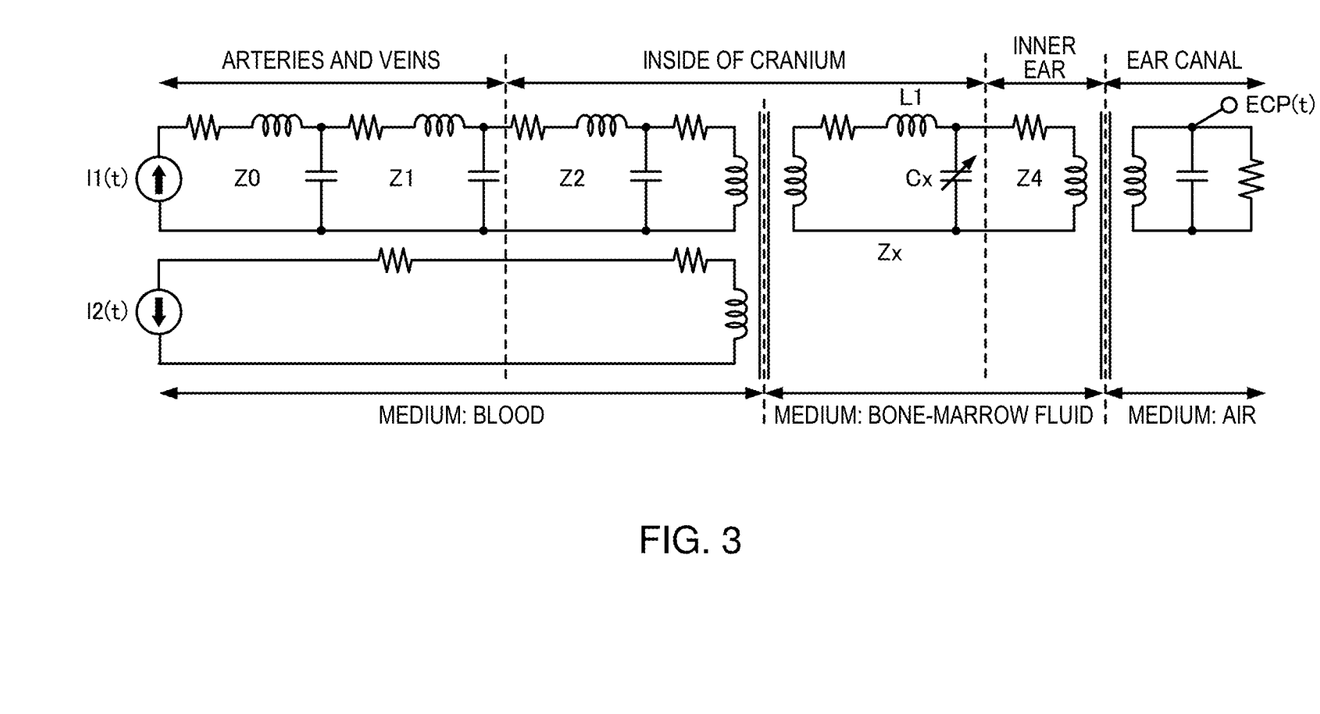
FIG. 3 is a diagram illustrating an equivalent circuit model that simulates pulse wave propagation from the carotid to the ear canal.
Figure 4:
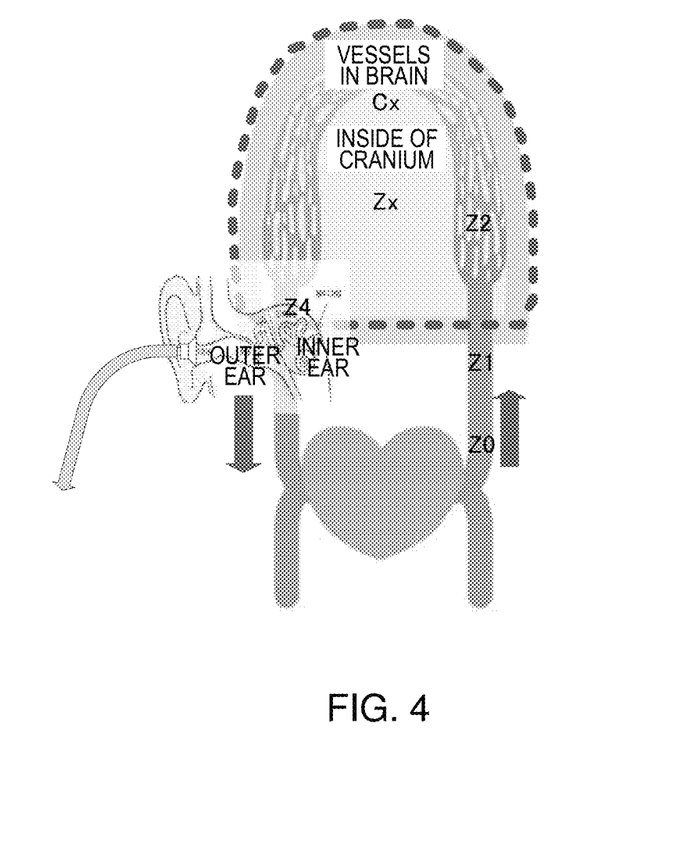
FIG. 4 is a diagram schematically illustrating the heart, the inside of the cranium, the inner ear, and the ear canal.

FIG. 3 is a diagram illustrating an equivalent circuit model that simulates pulse wave propagation from the carotid to the ear canal. FIG. 4 is a diagram schematically illustrating the heart, the inside of the cranium, the inner ear, and the ear canal. In the equivalent circuit model illustrated in FIG. 3, blood flow source pulse waves (artery) $11(t)$ and blood flow source pulse waves (vein) $12(t)$ are input as current, and the flow of media (blood, bone-marrow fluid, air) is simulated by current and pressure is simulated by voltage. The compliance is represented by a capacitor, the channel resistance is represented by a resistor, and the mass is represented by a coil. The blood inside the cranium and the bone-marrow fluid are insulated by a transformer and the inner ear and the ear canal (eardrum) are insulated by a transformer. ECP(t) in FIG. 3 represents the external ear canal pressure pulse wave sensor 10.

When it is supposed from the equivalent circuit model illustrated in FIG. 3 that an intracerebral substance minutely vibrates in the cranium due to the volume change in blood caused by heartbeat, a natural resonant frequency fo due to the compliance Cx in the cranium and the inertial mass L1 in the cranium is present.

When the natural resonant frequency fo is supposed to be a single resonant system as illustrated in FIG. 3, fo is given by the following Equation (1).

$$2\pi \cdot fo = 1/(L1 \cdot Cx)^{1/2} \quad (1)$$

From Equation (1), the compliance Cx in the cranium is expressed by the following Equation (2).

$$Cx = 1/\{L1 \cdot (2\pi \cdot fo)^2\} \quad (2)$$

The intracranial pressure ICP is given by the following Equation (3) based on the known relational expression between the intracranial pressure ICP and the compliance Cx inside the cranium.

$$ICP = \alpha 1 \cdot \ln(1/Cx) = \alpha 1 \cdot \ln(4\pi^2 \cdot L1 \cdot fo^2) \quad (3)$$

where $\alpha 1$ is a proportionality constant.

Figure 5A:
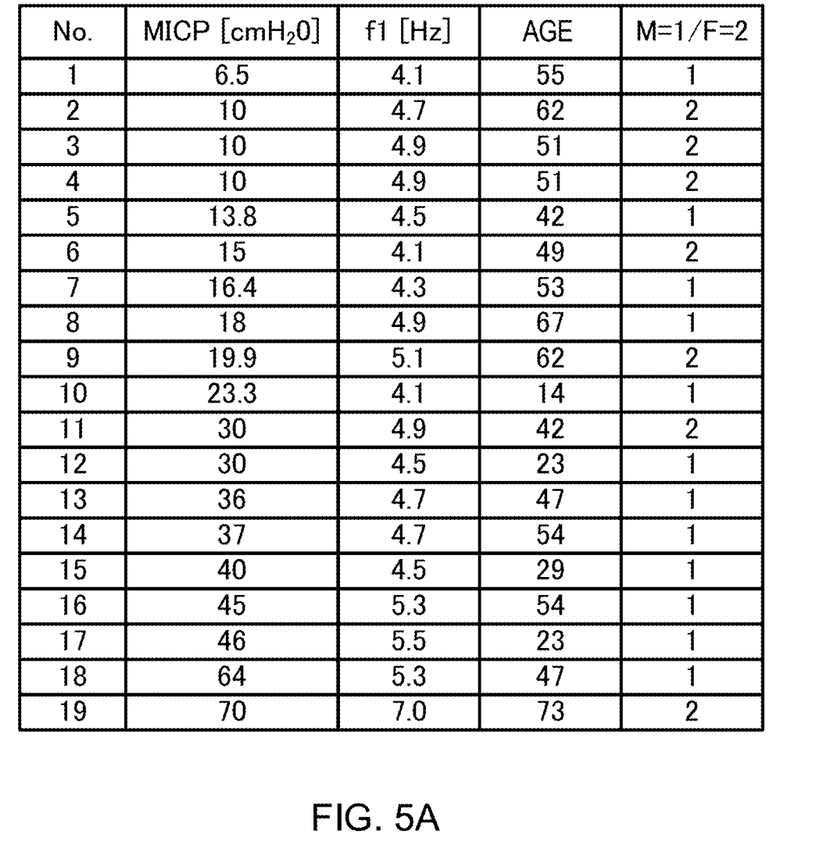
FIG. 5A is a table illustrating a relation of a measured value of intracranial pressure, a first formant frequency, age, and sex of nineteen subjects.
Figure 5B:
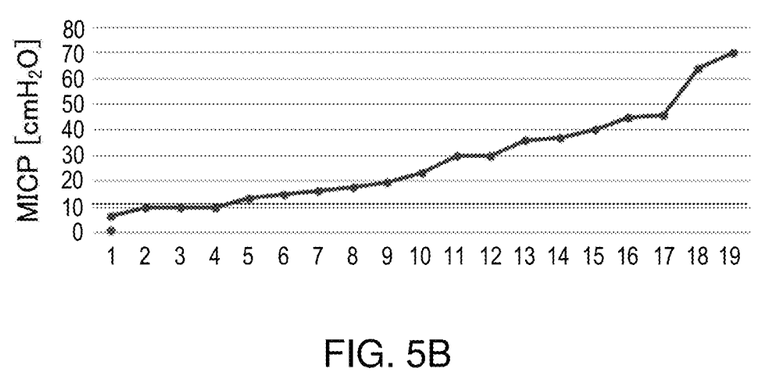
FIG. 5B is a graph illustrating measured values of intracranial pressure of nineteen subjects.
Figure 5C:
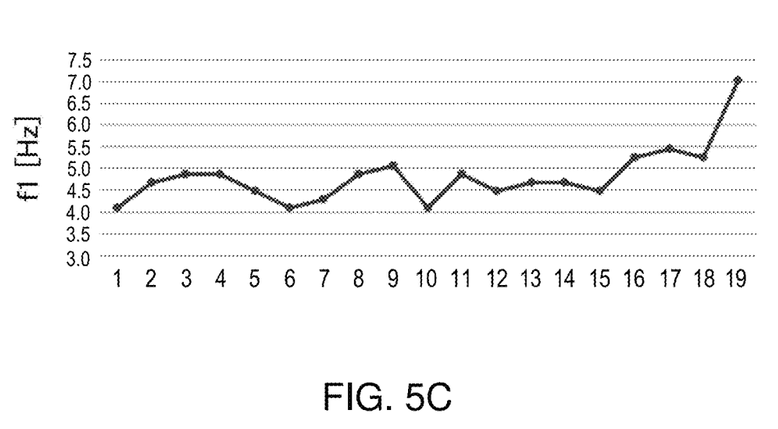
FIG. 5C is a graph illustrating first formant frequencies of nineteen subjects.
Figure 5D:
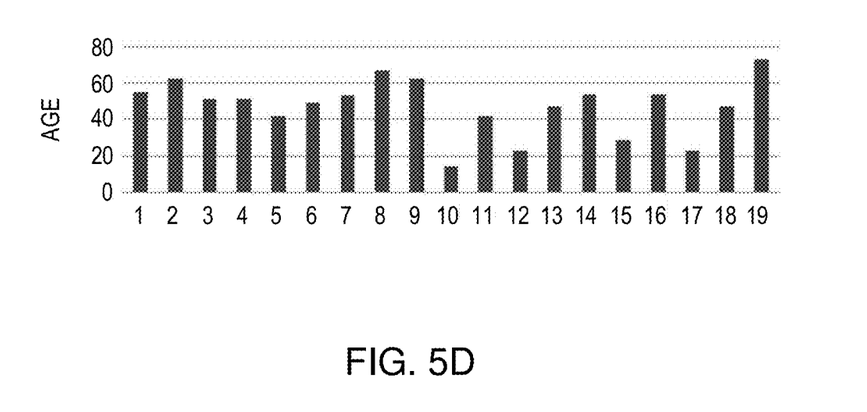
FIG. 5D is a graph illustrating the age of nineteen subjects.
Figure 5E:
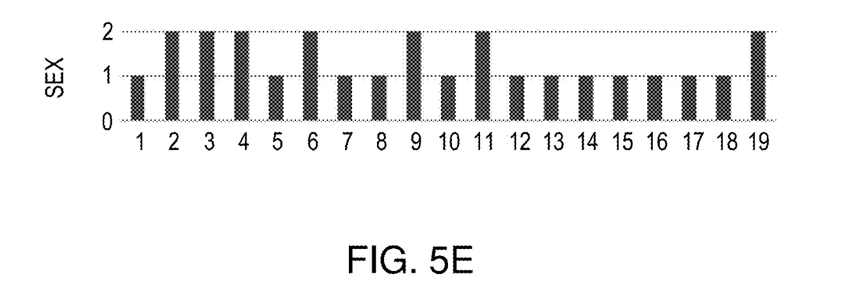
FIG. 5E is a graph illustrating the sex of nineteen subjects.

FIG. 5A is a table illustrating the relation among a measured value MICP (unit: $cmH_2O$) of the intracranial pressure, a first formant frequency f1 (unit: Hz), and age and sex (male=1, female=2) of nineteen subjects. FIG. 5B is a graph illustrating the measured value MICP of the intracranial pressure of each subject, FIG. 5C is a graph illustrating the first formant frequency f1 of each subject, FIG. 5D is a graph illustrating the age of each subject, and FIG. 5E is a graph illustrating the sex of each subject. The measured value MICP of the intracranial pressure was measured by using an intracranial pressure sensor (drainage pressure sensor or indwelling subdural space sensor). The first formant frequency f1 was determined by subjecting external ear canal pressure pulse wave data to high-pass filter processing for cutting signal components of 3 Hz or lower and performing linear predictive analysis (LPC analysis: 1,024 points (5.12 seconds), 20th order). f1 illustrated in FIG. 5A is an average value in a measurement period (about 10 minutes).

Figure 6:
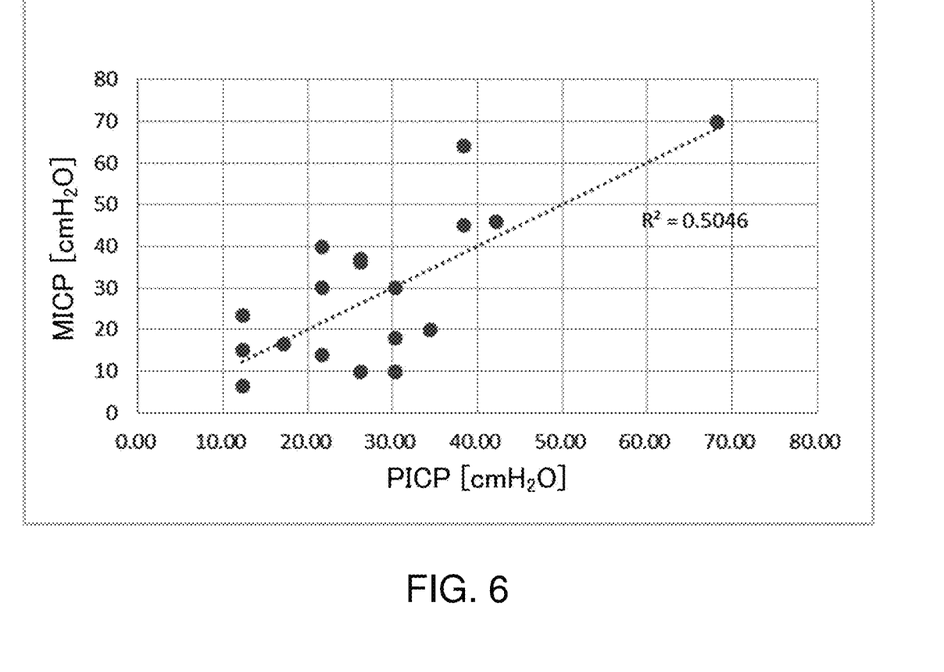
FIG. 6 is a graph illustrating a relation between an estimated value of intracranial pressure calculated by using an uncorrected first formant frequency and a measured value of the intracranial pressure.

The first formant frequency f1 illustrated in FIG. 5A was substituted into Equation (3) as fo to calculate an estimated value PICP of the intracranial pressure, and the estimated value PICP of the intracranial pressure was compared with the measured value MICP of the intracranial pressure illustrated in FIG. 5A. L1 in Equation (3) was a constant value. FIG. 6 illustrates the comparison results. The coefficient of determination $R^2$ (square of correlation coefficient) representing how well the estimated value PICP fits the measured value MICP when L1 is constant is 0.5046, which indicates that the correlation is low. The conceivable reason is that L1 differs depending on the age and the sex.

Thus, in the intracranial pressure estimating method in an embodiment of the invention, the first formant frequency f1 is corrected based on the age and the sex of the subject. Specifically, the first formant frequency f1 is corrected by the following Equation (4) to calculate a corrected value Xf1.

$$Xf1 = f1 + \beta 1 \cdot \ln(K/\text{Age}) + \beta 2 \cdot FM \quad (4)$$

where $\beta 1$, K, and $\beta 2$ are constants, and Age is the age. FM is the sex, which is 0 for male and 1 for female.

The corrected value Xf1 in Equation (4) is used to rewrite Equation (3), and the estimated value PICP of the intracranial pressure is given by the following Equation (5).

$$PICP = A \cdot \ln(Xf1) + B \quad (5)$$

where A and B are constants. For example, the constants in Equation (4) are set such that $\beta 1 = 1.5$, $\beta 2 = -0.4$, and $K = 50$, and the data (first formant frequency f1, age, and sex) illustrated in FIG. 5A are used to determine a corrected value Xf1 by Equation (4). The determined corrected value Xf1 and the measured value MICP of the intracranial pressure illustrated in FIG. 5A are used to perform linear regression analysis to determine optimal values of the constants in Equation (5). The determined optimal values are $A = 124.24$ and $B = -163.83$. For Age, the upper limit value and the lower limit value were provided, and Age was 30 for 30-year-old or younger subjects and 65 for 65-year-old or older subjects.

Figure 7:
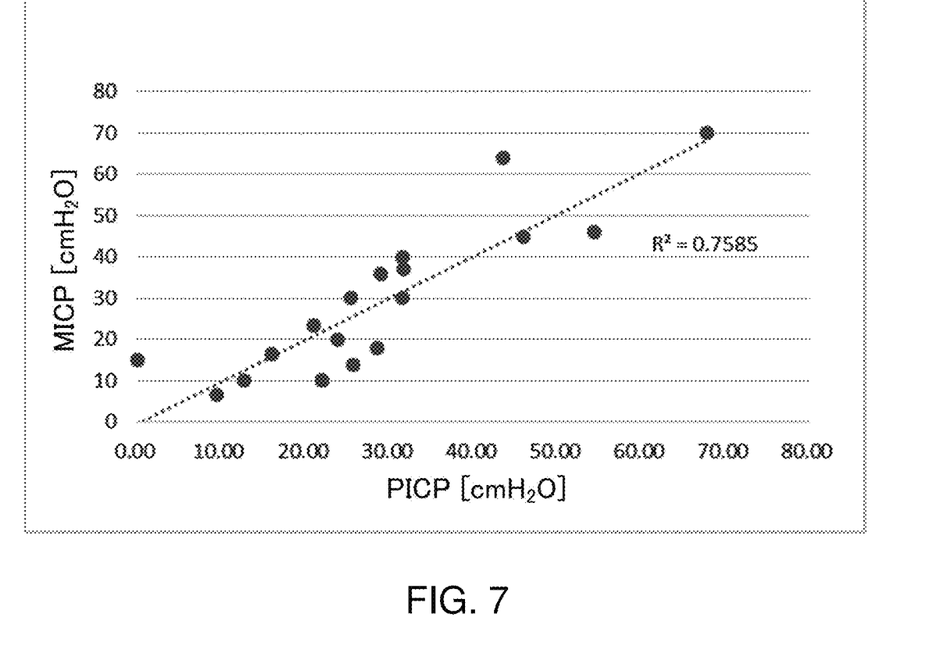
FIG. 7 is a graph illustrating a relation between an estimated value of intracranial pressure calculated by using a value obtained by correcting the first formant frequency and a measured value of the intracranial pressure.

The optimal values of the constants and the corrected value Xf1 obtained from the data illustrated in FIG. 5A were used to calculate the estimated value PICP of the intracranial pressure by Equation (5), and the calculated estimated value PICP of the intracranial pressure was compared with the measured value MICP of the intracranial pressure illustrated in FIG. 5A. FIG. 7 illustrates the comparison results. By calculating the estimated value PICP by using the corrected value Xf1 obtained by correcting the first formant frequency based on the age and the sex, the coefficient of determination $R^2$ representing how well the estimated value PICP fits the measured value MICP was improved to 0.7585. In this manner, it was confirmed that the estimation accuracy of the intracranial pressure could be improved by the intracranial pressure estimating method in an embodiment of the invention.

3. Processing

Figure 8:
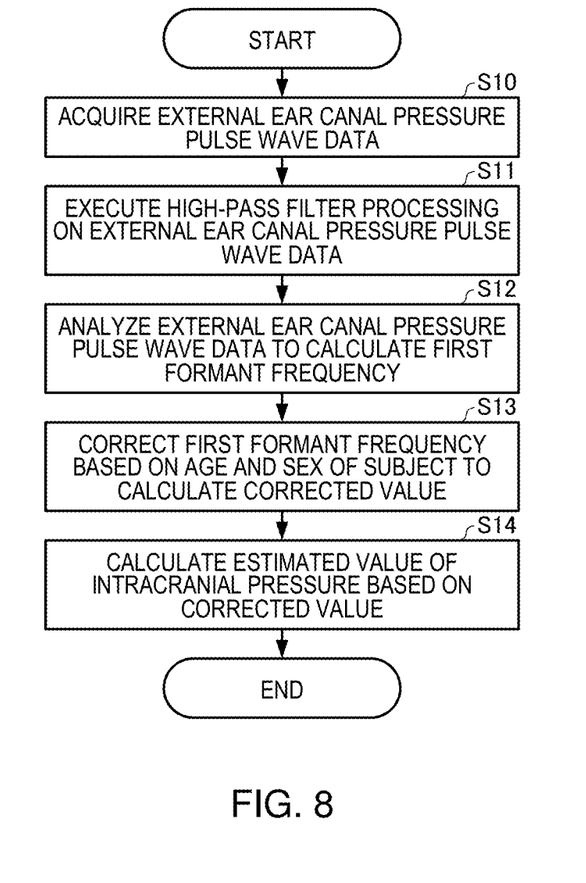
FIG. 8 is a flowchart illustrating the flow of processing of the intracranial pressure estimating device according to an embodiment of the invention.

FIG. 8 is a flowchart illustrating the flow of processing of the intracranial pressure estimating device 1.

First, the arithmetic unit 40 acquires external ear canal pressure pulse wave data obtained by digitalizing time-series data on external ear canal pressure pulse waves detected by the external ear canal pressure pulse wave sensor 10 (Step S10). Further, the arithmetic unit 40 acquires age Age and sex FM of a subject input from an input unit (not shown).

Next, the arithmetic unit 40 executes high-pass filter processing on the acquired external ear canal pressure pulse wave data (Step S11). For example, a high-pass filter for cutting frequencies of 3 Hz or lower can be applied to remove disturbance elements, such as breathing and heartbeat of the subject. Next, the arithmetic unit 40 analyzes the external ear canal pressure pulse wave data subjected to the high-pass filter processing (such as LPC analysis) to calculate a first formant frequency f1 (Step S12).

Next, the arithmetic unit 40 corrects the calculated first formant frequency f1 by Equation (4) based on the age Age and the sex FM of the subject to calculate a corrected value Xf1 (Step S13). Next, the arithmetic unit 40 calculates an estimated value PICP of the intracranial pressure by Equation (5) based on the calculated corrected value Xf1 (Step S14).

According to an embodiment of the invention, the intracranial pressure can be estimated based on external ear canal pressure pulse waves that can be measured by a non-invasive and simple device, and hence the intracranial pressure can be estimated in real time without purring burden on subjects. Further, the first formant frequency f1 of the external ear canal pressure pulse wave data is corrected based on the age and the sex of the subject, and the obtained corrected value Xf1 is used to calculate the estimated value PICP of the intracranial pressure. Thus, the intracranial pressure can be accurately estimated in consideration of the difference in inertial mass L1 in the cranium depending on the age and the sex of subjects.

While the embodiment or the modification has been described above, the invention is not limited to the embodiment or the modification, and can be carried out in various modes within the range not departing from the invention.

The invention includes configurations that are substantially the same as the configurations described in the embodiments (for example, a configuration having the same function, method and result or a configuration having the same objective and effect). The invention also includes configurations in which non-essential elements described in the embodiments have been replaced by other elements. The invention further includes configurations having the same effects as those of the configurations described in the embodiments, or configurations capable of achieving the same objectives as those of the configurations described in the embodiments. Moreover, the invention includes configurations in which known art is added to the configurations described in the embodiments.

REFERENCE SIGNS LIST

1 Intracranial pressure estimating device
10 External ear canal pressure pulse wave sensor
11 Sealed portion
12 Microphone
13 Sound hole
14 Sound hole
20 Amplifier
30 AD converter
40 Arithmetic unit
50 Display unit

The invention claimed is:

1. An intracranial pressure estimating method for estimating an intracranial pressure from time-series data on external ear canal pressure pulse waves, the method comprising:
   an acquisition step of acquiring time-series data on external ear canal pressure pulse waves of a subject from a microphone or a pressure sensor disposed within the subject's ear;
   an analysis step of analyzing external ear canal pressure pulse wave data obtained by digitalizing the time-series data on the external ear canal pressure pulse waves and calculating a first formant frequency of the external ear canal pressure pulse wave data by performing linear predictive analysis on the digitalized time-series data;

a correction step of correcting the first formant frequency based on age information and gender information for the subject to calculate a corrected value; and an estimation step of calculating an estimated value of an intracranial pressure based on the corrected value.

2. The intracranial pressure estimating method according to claim 1, wherein the analysis step includes analyzing data obtained by subjecting the external ear canal pressure pulse wave data to high-pass filter processing to calculate the first formant frequency.

3. The intracranial pressure estimating method according to claim 1, wherein the estimation step includes calculating an estimated value PICP of the intracranial pressure based on the following equation:

$$PICP = A \cdot \ln(Xf1) + B$$

where A and B are constants, and Xf1 is the corrected value.

4. The intracranial pressure estimating method according to claim 3, wherein the correction step includes calculating the corrected value Xf1 based on the following equation:

$$Xf1 = f1 + \beta1 \cdot \ln(K/Age) + \beta2 \cdot FM$$

where f1 is the first formant frequency, $\beta1$, K, and $\beta2$ are constants, Age is the age information of the subject, and FM is the gender information of the subject (0 for male and 1 for female).

5. The intracranial pressure estimating method according to claim 1, further comprising a display step of displaying the estimated value of the intracranial pressure on a display.

6. An intracranial pressure estimating device comprising:

an external ear canal pressure pulse wave sensor that detects external ear canal pressure pulse waves of a subject, the sensor being configured to be disposed within the subject's ear; and an arithmetic unit that estimates an intracranial pressure from time-series data on the external ear canal pressure pulse waves, wherein the arithmetic unit analyzes external ear canal pressure pulse wave data obtained by digitalizing the time-series data on the external ear canal pressure pulse waves, calculates a first formant frequency of the external ear canal pressure pulse wave data by performing linear predictive analysis on the digitalized time-series data, corrects the first formant frequency based on age information and gender information for the subject to calculate a corrected value, and calculates an estimated value of the intracranial pressure based on the corrected value.

7. The intracranial pressure estimating device according to claim 6, further comprising a display that displays the estimated value of the intracranial pressure.

8. An intracranial pressure estimating device comprising:

a microphone or a pressure sensor configured to detect external ear canal pressure pulse waves of a subject, the microphone or the pressure sensor being configured to be disposed within the subject's ear; and a processor programmed to estimate an intracranial pressure from time-series data on the external ear canal pressure pulse waves, wherein the processor analyzes external ear canal pressure pulse wave data obtained by digitalizing the time-series data on the external ear canal pressure pulse waves, calculates a first formant frequency of the external ear canal pressure pulse wave data by performing linear predictive analysis on the digitalized time-series data, corrects the first formant frequency based on age information and gender information for the subject to calculate a corrected value, and calculates an estimated value of the intracranial pressure based on the corrected value.

9. The intracranial pressure estimating device according to claim 8, further comprising a display that displays the estimated value of the intracranial pressure.

* * * * *